United States Patent [19]

Fujimoto et al.

[11] 4,263,437
[45] * Apr. 21, 1981

[54] ACETIC ACID DERIVATIVES OF 5,6-DIHYDROBENZO[b]PYRIDO[3,2-f]THIEPINE AND OXEPINE

[75] Inventors: Yasuo Fujimoto, Tokyo; Shigeru Yamabe, Kobe, both of Japan

[73] Assignee: Nippon Chemiphar Co., Ltd., Tokyo, Japan

[ * ] Notice: The portion of the term of this patent subsequent to May 27, 1997, has been disclaimed.

[21] Appl. No.: 15,610

[22] Filed: Feb. 27, 1979

[30] Foreign Application Priority Data

Mar. 1, 1978 [JP] Japan ................. 53/22097

[51] Int. Cl.³ .................. C07D 491/44; C07D 495/04
[52] U.S. Cl. ..................... 546/89; 546/80; 549/12; 260/333; 424/256; 424/275; 424/278
[58] Field of Search ........................ 546/80, 89

[56] References Cited

U.S. PATENT DOCUMENTS

| | | | |
|---|---|---|---|
| 3,931,205 | 1/1976 | Nakanishi et al. | 546/80 |
| 4,025,640 | 7/1977 | McFadden et al. | 424/275 |
| 4,101,667 | 7/1978 | Yamabe et al. | 549/12 |
| 4,104,280 | 8/1978 | Ackrell | 549/12 |
| 4,205,170 | 5/1980 | Fujimoto et al. | 546/89 |

OTHER PUBLICATIONS

Hackh's Chemical Dictionary, 4th Ed., McGraw Hill, New York, 1969, p. 27.

Primary Examiner—Henry R. Jiles
Assistant Examiner—Natalia Harkaway
Attorney, Agent, or Firm—Oblon, Fisher, Spivak, McClelland & Maier

[57] ABSTRACT

Acetic acid derivatives having the formula,

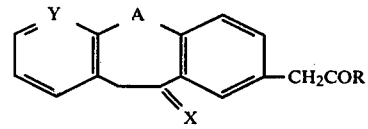

wherein X represents an oxygen or two hydrogen atoms, Y represents CH or N, A represents an oxygen or sulfur atom, and R represents hydroxy, amino or a lower alkoxy group having 1 to 5 carbon atoms possess excellent antiinflammatory activities.

8 Claims, No Drawings

ACETIC ACID DERIVATIVES OF 5,6-DIHYDROBENZO[b]PYRIDO[3,2-f]THIEPINE AND OXEPINE

BACKGROUND OF THE INVENTION

This invention relates to novel acetic acid derivatives and to a process for producing the same.

The present inventors have studied a wide variety of compounds, and as a result of this study, they have found acetic acid derivatives which exhibit excellent antiinflammatory activities.

SUMMARY OF THE INVENTION

It is, therefore, one object of this invention to provide novel acetic acid derivatives represented by the formula (I).

It is another object of the invention to provide acetic acid derivatives of the formula (I) possessing strong antiinflammatory action.

It is a further object of the invention to provide a novel process for producing the acetic acid derivatives of the formula (I).

The present inventors have studied a wide variety of compounds, and as a result of this study, they have found that the acetic acid derivatives of the formula (I),

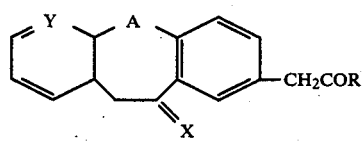

(I)

wherein X represents an oxygen or two hydrogen atoms, Y represents CH or N, A represents an oxygen or sulfur atom, and R represents hydroxy, amino or a lower alkoxy group having 1 to 5 carbon atoms, exhibit excellent antiinflammatory activities.

DETAILED DESCRIPTION OF THE PREFERRED EMBODIMENTS

The compounds of the formula (I) are divided into the following groups of the formulae (II) and (III).

(II)

(III)

wherein A, X and R are the same as defined above.

The compounds of the formulae (II) and (III) are further divided into the following groups of the formulae (IV) and (V) and the formulae (VI) and (VII), respectively.

(IV)

(V)

(VI)

(VII)

wherein X and R are the same as defined above.

The compounds of the formula (IV) are substituted into the following groups of the formulae (VIII) and (IX).

(VIII)

(IX)

wherein R is the same as defined above.

The compounds of the formula (V) are substituted into the following groups of the formulae (X) and (XI).

(X)

(XI)

wherein R is the same as defined above.

The compounds of the formula (VI) are subdivided into the following groups of the formulae (XII) and (XIII).

(XII)

-continued (XIII) [Structure: bicyclic with N, S heteroatoms, substituent —CH₂COR]

wherein R is the same as defined above.

The compounds of the formula (VII) are subdivided into the following groups of the formulae (XIV) and (XV).

(XIV) [Structure: tricyclic with N, O, substituent —CH₂COR, ketone]

(XV) [Structure: tricyclic with N, O, substituent —CH₂COR]

wherein R is the same as defined above.

Of the above compounds particularly preferable are the compounds having the formulae (VIII), (XI), (XIII) and (XV).

According to the present invention, the compounds of the formula (I) are produced by any one of the processes as hereinafter disclosed.

Process 1

(XVI) [Structure: Y-ring-A-phenyl-CH₂R₂, with CH₂-COOH side chain] →

(XVII) [Structure: cyclized tricyclic Y, A with —CH₂CONH₂ and ketone]

wherein $R_2$ represents a carbamoyl or cyano group, and Y and A are the same as defined above.

According to process 1, the compounds of the formula (XVII) are produced by cyclizing the compounds of the formula (XVI) or active derivatives thereof in the presence of a condensing agent.

Suitable condensing agents which are useful in this invention include, for example, polyphosphoric acid, polyphosphoric acid ester and the like. The reaction is preferably conducted for 0.5 to 4 hours at 80° to 180° C. with or without a solvent such as benzene, toluene or xylene.

Process 2

(XVIII) [Structure: Y-ring-A-phenyl-CH₂COOH, with CH₂-COOH side chain] →

(IXX) [Structure: cyclized tricyclic with —CH₂COOH and ketone]

wherein Y and A are the same as defined above.

According to process 2, the compounds of the formula (IXX) are produced by cyclizing the compounds of the formula (XVIII) or active derivatives thereof in the presence of a condensing agent.

This reaction is carried out by the same procedure as process 1.

The starting materials of the formulae (XVI) and (XVIII) are produced by the following scheme.

(XX) [Y-ring-B + CH₂/COOR₄ side chain] + (XXI) [C—phenyl—CHO] →

(XXII) [Y-A-phenyl-CHO, CH₂/COOR₄ side chain] →

(XXIII) [Y-A-phenyl-CH₂OH, CH₂/COOR₄ side chain] →

(XXIV) [Y-A-phenyl-CH₂Z, CH₂/COOR₄ side chain] →

(XXV) [Y-A-phenyl-CH₂CN, CH₂/COOR₄ side chain] → (XVI)' [Y-A-phenyl-CH₂CN, CH₂/COOH side chain]

(XVI)'' [Y-A-phenyl-CH₂CONH₂, CH₂/COOH side chain]

(XVIII) [Y-A-phenyl-CH₂COOH, CH₂/COOH side chain]

wherein Y and A are the same as defined above, B and C represent a halogen atom, a hydroxy or mercapto group or a metallic salt thereof wherein B is a halogen atom when C is a hydroxy or mercapto group or a metallic salt thereof, and B is a hydroxy or mercapto group or a metallic salt thereof when C is a halogen atom, Z represents a halogen atom, and R₄ represents an ester residue.

More specifically, the compounds of the formula (XX) are reacted with the compounds of the formula (XXI) to produce the compounds of the formula (XXII), which are reduced to obtain the compounds of the formula (XXIII), which are halogenated to obtain the compounds of the formula (XXIV), which are reacted with a metallic cyanide to obtain the compounds of the formula (XXV), which are hydrolyzed, thereby yielding the compounds of the formula (XVI)', (XVI)'' or (XVIII).

The compounds of the formula (XVIII) may be produced by the following scheme.

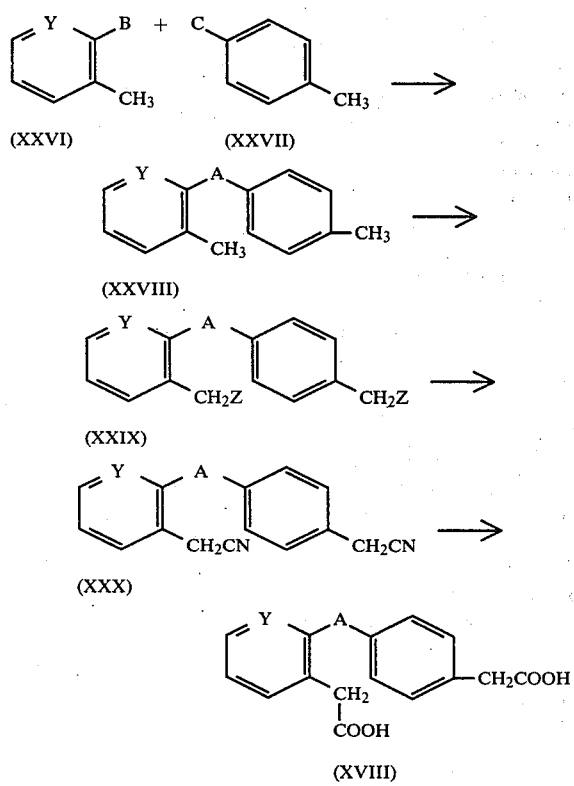

wherein A, B, C, Y and Z are the same as defined above.

The compounds of the formula (XXVI) are reacted with the compounds of the formula (XXVII) to obtain the compounds of the formula (XXVIII), which are halogenated to obtain the compounds of the formula (XXIX), which are reacted with a metallic cyanide to obtain the compounds of the formula (XXX), which are hydrolyzed, whereby the compounds of the formula (XVIII) are obtained.

Process 3

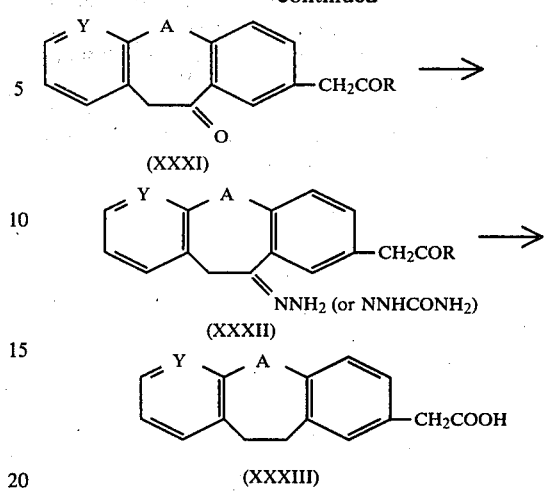

wherein A, Y and R are the same as defined above.

According to process 3, the compounds of the formula (XXXIII) are produced by reacting the compounds of the formula (XXXI) with hydrazine or semicarbazide, and reacting the resulting hydrazone or semicarbazone of the formula (XXXII) with an alkaline agent.

In producing the compounds of the formula (XXXII) from the compounds of the formula (XXXI), the reaction may be conducted without any solvent, but is preferably carried out in an organic solvent, for example, an alcohol such as methanol or ethanol, and an ether such as dioxane or tetrahydrofuran for 1 to 8 hours under reflux conditions.

In producing the compounds of the formula (XXXIII) from the compounds of the formula (XXXII), the compounds of the formula (XXXII) are reacted with an alkaline agent in an inert solvent, for example, an alcohol such as ethanol, t-butanol or diethylene glycol, which does not participate in the reaction, and an ether such as dioxane or tetrahydrofuran, preferably in diethylene glycol at 60° to 200° C. for 1 to 4 hours.

Alkaline agents which are useful in the invention include, for example, potassium hydroxide, sodium hydroxide and metallic alkoxides.

Process 4

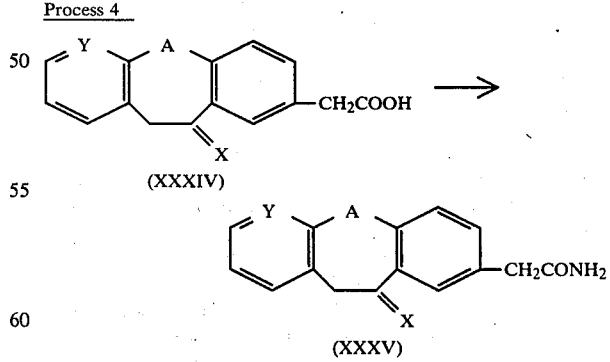

wherein A, X and Y are the same as defined above.

According to process 4, the compounds of the formula (XXXV) are produced by reacting the compounds of the formula (XXXIV) or reactive derivatives thereof with ammonia. The reactive derivatives of the formula (XXXIV) include acid halides, mixed acid anhydrides and activated esters. The reaction may be conducted in an inert solvent such as chloroform, methylene chloride, benzene, toluene or tetrahydrofuran, which does not participate in the reaction, at 0° C. to the boiling point of the solvent for 1 to 20 hours. When the free acetic acid derivatives of the formula (XXXIV) are employed, a condensing agent such as dicyclohexyl carbodiimide may be used.

Process 5

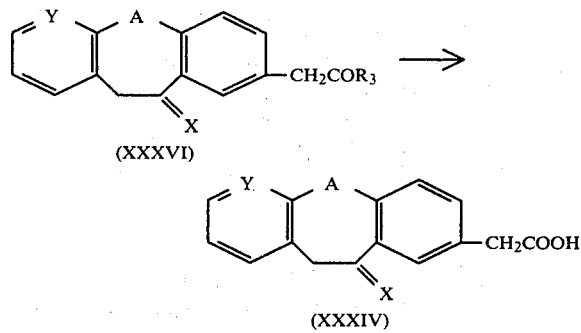

wherein $R_3$ represents an amino or lower alkoxy group having 1 to 5 carbon atoms, and X, Y and A are the same as defined above.

According to process 5, the compounds of the formula (XXXIV) are produced by hydrolyzing the compounds of the formula (XXXVI).

This reaction is carried out by the usual method; that is, the reaction is preferably conducted in water or a solvent containing some water, for example, an alcohol such as methanol or ethanol in the presence of a catalyst such as potassium hydroxide, sodium hydroxide, hydrochloric acid or sulfuric acid at temperatures from room temperature to the boiling point of the solvent.

Process 6

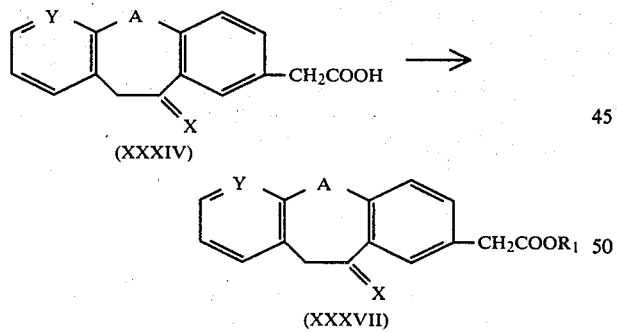

wherein $R_1$ represents a lower alkyl group having 1 to 5 carbon atoms, and X, Y and A are the same as defined above.

According to process 6, the compounds of the formula (XXXVII) are produced by reacting the compounds of the formula (XXXIV) with an alcohol having 1 to 5 carbon atoms or a reactive derivative thereof. The reactive derivatives of the alcohol include diazoalkanes such as diazomethane. The reaction is conducted in an alcohol $R_1OH$ ($R_1$ is the same as defined above) with the use of a mineral acid such as sulfuric acid or hydrochloric acid at temperatures from room temperature to the boiling point of the solvent for 1 to 15 hours. When the diazoalkane is used, the reaction is conducted in an ether solution containing the diazoalkane such as diazomethane at 0° C. to room temperature.

The compounds of this invention exhibit both oral and parenteral activities and can be formulated in dosage forms for oral, parenteral, rectal or topical administration. Solid dosage forms for oral administration include capsules, tablets, pills, powders and granules. In these solid dosage forms, the active compounds are admixed with at least one inert diluent such as sucrose, lactose or starch. Such dosage forms comprise, as is in the normal practice, an additional substance other than the inert diluent, e.g., a lubricating agent such as magnesium stearate. In the case where the compounds are used in the forms of capsules, tablets and pills, a buffering agent can be further employed. The tablets and pills can additionally be prepared with an enteric coating.

Liquid dosage forms for oral administration include pharmaceutically acceptable emulsions, solutions, suspensions, syrups and elixirs containing inert diluents commonly used in the art such as purified water and alcohols. In addition to the inert diluents, compositions including adjuvants such as wetting agents, emulsifying and suspending agents, and sweetening, flavoring and perfuming agents may be utilized in this invention. The preparations according to this invention for parenteral administration include sterile aqueous or non-aqueous solutions, suspensions or emulsions. Examples of the non-aqueous solvents or vehicles are propylene glycol, polyethylene glycol, vegetable oils such as olive oil, and injectable organic esters such as ethyl oleate. The compositions for rectal administration are suppositories which may contain, besides the active substances, excipients such as cocoa butter or a suppository wax.

The dosages of active ingredients in the compositions of this invention may be varied; however, it is necessary that the amount of the active ingredients be such that any one suitable dosage form is attained. The selected dosage depends upon the desired therapeutic effect, administration route and treatment duration. Generally, the dosage levels between 0.4 to 20 mg/kg of body weight are daily administered to mammals to obtain effective relief of inflammation.

The compounds of the present invention represented by the formula (I) possess excellent antiinflammatory effects.

Male Wistar rats each weighing about 100 g, one group consisting of 5 to 7 animals, were orally given the compounds according to this invention, and edema was induced in the hind paws by subcutaneous injections of 0.1 ml of 1% carrageenan one hour after the administration of the test compounds. Thereafter, the volumes of the hind paws were measured by a volume differential meter. The results obtained are shown in Table 1.

TABLE 1

| Test Compounds | Dosage (mg/kg) | Inhibition (%) (3 hours) |
|---|---|---|
| Compound 1 | 5 | 58.0 |
| 2 | 5 | 42.1 |
| 3 | 5 | 50.6 |
| 4 | 5 | 45.3 |
| 5 | 5 | 46.0 |
| 6 | 5 | 44.1 |
| 7 | 5 | 47.9 |
| 8 | 5 | 61.4 |
| 9 | 5 | 63.4 |
| 10 | 5 | 38.4 |
| 11 | 5 | 59.7 |
| 12 | 5 | 43.9 |
| 13 | 5 | 64.6 |

TABLE 1-continued

| Test Compounds | Dosage (mg/kg) | Inhibition (%) (3 hours) |
|---|---|---|
| 14 | 5 | 50.6 |
| 15 | 5 | 41.6 |
| Phenylbutazone | 5 | 20.9 |
| Flufenamic acid | 5 | 29.3 |

Compound
1:(10,11-Dihydro-11-oxo dibenzo[b,f]thiepin-2-yl)-acetic acid
2:(10,11-Dihydro-11-oxo dibenzo[b,f]thiepin-2-yl)-acetamide
3:Ethyl(10,11-dihydro-11-oxo dibenzo[b,f]thiepin-2-yl)-acetate
4:(10,11-Dihydro dibenzo[b,f]thiepin-2-yl)-acetic acid
5:Ethyl(10,11-dihydro dibenzo[b,f]thiepin-2-yl)-acetate
6:(10,11-Dihydro-11-oxo dibenzo[b,f]oxepin-2-yl)-acetic acid
7:Ethyl(10,11-oxo dibenzo[b,f]oxepin-2-yl)-acetate
8:(10,11-Dihydro dibenzo[b,f]oxepin-2-yl)-acetic acid
9:Ethyl(10,11-dihydro dibenzo[b,f]oxepin-2-yl)-acetate
10:Methyl(5,6-dihydro-6-oxo benzo[b]pyrido-[3,2-f]thiepin-8-yl)-acetate
11:(5,6-Dihydro benzo[b]pyrido[3,2-f]thiepin-8-yl)-acetic acid
12:(5,6-Dihydro benzo[b]pyrido[3,2-f]thiepin-8-yl)-acetamide
13:Ethyl(5,6-dihydro benzo[b]pyrido[3,2-f]-thiepin-8-yl)-acetate
14:(5,6-Dihydro benzo[b]pyrido[3,2-f]oxepin-8-yl)-acetic acid
15:Ethyl(5,6-dihydro benzo[b]pyrido[3,2-f]oxepin-8-yl)-acetate As can be seen from the results of Table 1, the present compounds possess excellent activities; in particular, the compounds of the formulae (VIII), (XI), (XIII) and (XV) are significantly effective in comparison with Phenylbutazone and Flufenamic acid which are widely used as antiinflammatory drugs.

The invention is illustrated below in further detail with reference to several Examples, but the invention is not limited to these Examples.

EXAMPLE 1

(10,11-Dihydro-11-oxo dibenzo[b,f]thiepin-2-yl)-acetic acid

To 50 mg of 2,4'-dicarboxymethyl-diphenylthioether was added 2.5 g of polyphosphoric acid, and the mixture was stirred under a dry atmosphere at 106° C. for 1.5 hours. After cooling, water was added to the mixture which was then extracted with ethyl acetate. The extract was washed with a 1% sodium hydroxide solution and then with a saturated sodium chloride solution and dried over anhydrous sodium sulfate. The solvent was distilled off under reduced pressure to obtain 36 mg of brown crystals, which were chromatographed over 7 g of silica gel and eluted with benzene acetone (10/11) to yield light red crystals. These crystals were recrystallized from a solvent of acetone, benzene and n-hexane to yield 28 mg (yield: 60%) of (10,11-dihydro-11-oxo dibenzo[b,f]thiepin-2-yl)-acetic acid as pale yellow crystals having a melting point of 166°–167° C.

IR $\nu_{max}^{KBr}$ cm$^{-1}$: 1700, 1675 (C=O).

NMR ((CD$_3$)$_2$CO)$\delta$: 3.67 (2H, s, —CH$_2$COOH), 4.33 (2H, s, —CH$_2$CO), 7.12–7.69 (6H, m, aromatic protons), 8.03 (1H, d, J=2 Hz, C$_1$H), MS m/e: 284 (M+).

EXAMPLE 2

(10,11-Dihydro-11-oxo dibenzo[b,f]thiepin-2-yl)-acetamide

To a mixture of 100 mg of (10,11-dihydro-11-oxo dibenzo[b,f]thiepin-2-yl)-acetic acid and 5 ml of dry tetrahydrofuran were added 0.2 g of oxalyl chloride and a drop of dimethylformamide, and the mixture was stirred with ice cooling for 2 hours. To this was added 10 ml of tetrahydrofuran containing 1% ammonia, and the mixture was stirred at room temperature for 14 hours. After the completion of the reaction, to this mixture were added water and 2 N hydrochloric acid for acidification, and the resulting mixture was extracted with ethyl acetate. The extract was washed with a 1% sodium hydroxide solution and then with a saturated sodium chloride solution and dried over anhydrous sodium sulfate. The solvent was distilled off under reduced pressure to obtain 78 mg of light yellow crystals, which were recrystallized from a solvent of chloroform and n-hexane to give 55 mg (yield: 55%) of (10,11-dihydro-11-oxo dibenzo[b,f]thiepin-2-yl)-acetamide as pale yellow crystals having a melting point of 171°–172.5° C.

IR $\nu_{max}^{KBr}$ cm$^{-1}$: 3380, 3180 (NH$_2$), 1670 (C=O).

NMR (CDCl$_3$+(CD$_3$)$_2$CO)$\delta$: 3.50 (2H, s, —CH$_2$CONH$_2$), 4.30 (2H, s, —CH$_2$CO), 6.04, 6.78 (2H, b.sx2, —CONH$_2$), 6.96–7.66 (6H, m, aromatic protons), 7.98 (1H, d, J=2 Hz, C$_1$H).

EXAMPLE 3

Ethyl(10,11-dihydro-11-oxo dibenzo[b,f]thiepin-2-yl)-acetate 70 mg of (10,11-dihydro-11-oxo dibenzo[b,f]thiepin-2-yl)-acetic acid was dissolved in 3 ml of ethanol containing 7% hydrogen chloride, and the resulting mixture was stirred under a dry atmosphere at room temperature for 2 hours. To this was added water, and the mixture was extracted with ethyl acetate. The extract was washed with a saturated sodium hydrogen carbonate solution and then with a saturated sodium chloride solution and dried over anhydrous sodium sulfate. The solvent was removed by distillation under reduced pressure to obtain a residue, which was chromatographed over 7 g of silica gel and eluted with n-hexane/acetone (10/1).

The elute was again chromatographed over 10 g of silica gel and eluted with benzene, thereby obtaining a pale yellow oil. This oil was recrystallized to yield 43 mg (yield: 56%) of ethyl(10,11-dihydro-11-oxo dibenzo[b,f]thiepin-2-yl)-acetate as colorless crystals having a melting point of 60°–62° C.

IR $\nu_{max}^{KBr}$ cm$^{-1}$: 1740, 1680 (C=O).

NMR (CDCl$_3$)$\delta$:1.21 (3H, t, J=8 Hz, —CH$_2$CH$_3$), 3.58 (2H, s, —CH$_2$COO), 4.11 (2H, q, J=8 Hz, —CH$_2$CH$_3$), 4.33 (2H, s, —CH$_2$CO—), 7.02–7.66 (6H, m, aromatic protons), 8.07 (1H, s, C$_1$H).

EXAMPLE 4

(10,11-Dihydro dibenzo[b,f]thiepin-2-yl)-acetic acid

To 400 mg of (10,11-dihydro-11-oxo dibenzo[b,f]thiepin-2-yl)-acetic acid were added 20 ml of ethanol and 1 ml of hydrazine hydrate, and the mixture was refluxed with stirring under a dry atmosphere for 5 hours. After cooling, the solvent was removed by distillation under reduced pressure, and to the resulting mixture were added 20 ml of diethylene glycol and 4.0 g of sodium hydroxide. Thereafter, the resulting mixture was stirred under a dry atmosphere at 130° C. for 2 hours. After subsequent cooling, water was added to the mixture which was then washed with ethyl acetate. The aqueous layer was acidified with hydrochloric acid and extracted with ethyl acetate. The extract was washed with a saturated sodium chloride solution and dried over anhydrous sodium sulfate. The solvent was distilled off under reduced pressure to obtain a residue, which was chromatographed over 18 g of silica gel and eluted with n-hexane/acetone (5/1) to obtain pale yellow crystals. These crystals were recrystallized from acetone/n-hexane to give 321 mg (yield: 84%) of (10,11- dihydro dibenzo[b,f]thiepin-2-yl)-acetic acid as colorless crystals having a melting point of 111°–112° C.

IR $\nu_{max}^{KBr}$ cm$^{-1}$: 1715 (C=O).

NMR (CDCl$_3$) δ: 3.31 (4H, s, —C$\underline{H}_2$C$\underline{H}_2$—), 3.55 (2H, s, —C$\underline{H}_2$COOH), 6.90–7.50 (7H, m, aromatic protons).

MS m/e: 270 (M+).

EXAMPLE 5

(10,11-Dihydro dibenzo[b,f]thiepin-2-yl)-acetamide

To 100 mg of (10,11-dihydro dibenzo[b,f]thiepin-2-yl)-acetic acid in 5 ml of dry tetrahydrofuran were added 0.2 g of oxalyl chloride and a drop of dimethylformamide, and the mixture was stirred with ice cooling under a dry atmosphere for 3 hours. To the mixture was added 5 ml of tetrahydrofuran containing 1% ammonia, and the mixture was stirred under a dry atmosphere at room temperature for 14 hours. After the addition of water, the mixture was extracted with ethyl acetate. The extract was washed with a 1% sodium hydroxide solution and then with a saturated sodium chloride solution and dried over anhydrous sodium sulfate. The solvent was distilled off under reduced pressure to obtain a residue, which was recrystallized from ethyl acetate, thereby obtaining 66 mg (yield: 66%) of (10,11-dihydro dibenzo[b,f]thiepin-2-yl)-acetamide as colorless crystals having a melting point of 188°–189° C.

IR $\nu_{max}^{KBr}$ cm$^{-1}$: 3350, 3180 (NH$_2$), 1665 (C=O).

NMR (CDCl$_3$+(CD$_3$)$_2$CO)δ 3.30 (4H, s, —C$\underline{H}_2$C$\underline{H}_2$—), 3.42 (2H, s, —C$\underline{H}_2$CO—), 6.90–7.40 (7H, m, aromatic protons).

EXAMPLE 6

Ethyl(10,11-dihydro dibenzo[b,f]thiepin-2-yl)-acetate

To 70 mg of (10,11-dihydro dibenzo[b,f]thiepin-2-yl)-acetic acid was added 3 ml of ethanol containing 7% hydrogen chloride, and the mixture was stirred under a dry atmosphere at room temperature for 2 hours. To this was added water, and the mixture was extracted with ethyl acetate. The extract was washed with a saturated sodium hydrogen carbonate solution and then with a saturated sodium chloride solution and dried over anhydrous sodium sulfate. The solvent was removed by distillation under reduced pressure to obtain a residue, which was chromatographed over 7 g of silica gel and eluted with n-hexane/acetone (10/1), thereby yielding 70 mg (yield: 91%) of ethyl (10,11-dihydro dibenzo[b,f]thiepin-2-yl)-acetate as a yellow oil.

IR $\nu_{max}^{KBr}$ cm$^{-1}$: 1730 (C=O).

NMR (CDCl$_3$)δ: 1.22 (3H, t, J=7 Hz, —CH$_2$C$\underline{H}_3$), 3.30 (4H, s, —C$\underline{H}_2$C$\underline{H}_2$—), 3.49 (2H, s, —C$\underline{H}_2$CO—), 4.10 (2H, g, J=7 Hz, —C$\underline{H}_2$CH$_3$), 6.80–7.45 (7H, m, aromatic protons).

EXAMPLE 7

(10,11-Dihydro-11-oxo dibenzo[b,f]oxepin-2-yl)-acetamide (a) To 59 mg of 2-(4-carbamoylmethylphenoxy)-phenylacetic acid was added 1.8 g of polyphosphoric acid, and the mixture was stirred under a dry atmosphere at 100° C. for 50 minutes. After being cooled, the resulting mixture was dissolved in water and then extracted with ethyl acetate. The extract was washed with a 1% sodium hydroxide solution and then with a saturated sodium chloride solution and dried over anhydrous sodium sulfate. The solvent was distilled off to obtain a residue, which was recrystallized from acetone/n-hexane to give 45 mg (yield: 76%) of (10,11-dihydro-11-oxo dibenzo[b,f]oxepin-2-yl)-acetamide as light yellow crystals having a melting point of 151.5°–154° C.

IR $\nu_{max}^{KBr}$ cm$^{-1}$: 3410, 3350 (NH$_2$), 1685, 1655 (C=O).

NMR (CDCl$_3$)δ: 3.51 (2H, s, —C$\underline{H}_2$—), 4.04 (2 H, s, —C$\underline{H}_2$—), 5.50 (2H, broad s, N$\underline{H}_2$), 7.05–7.50 (6H, m, aromatic protons), 7.87 (1H, d, J=2 Hz, C$_1\underline{H}$).

MS m/e: 267 (M+).

(b) To 208 mg of 2-(4-cyanomethylphenoxy)phenylacetic acid was added 4 mg of polyphosphoric acid, and the mixture was stirred under a dry atmosphere at 100° C. for 2 hours. After the completion of the reaction, the same procedure was repeated as in (a), whereby 160 mg (yield: 77%) of (10,11-dihydro-11-oxo dibenzo[b,f]oxepin-2-yl)-acetamide was obtained as light yellow crystals. The results of IR, NMR and MS are the same as defined in (a).

EXAMPLE 8

(10,11-dihydro-11-oxo dibenzo[b,f]oxepin-2-yl)-acetic acid

To a mixture of 2 ml of water, 2 ml of ethanol and 0.4 g of potassium hydroxide was added 100 mg of (10,11-dihydro-11-oxo dibenzo[b,f]oxepin-2-yl)-acetamide, and the resulting mixture was refluxed with stirring for 5 hours. After cooling, to this was added water, and the mixture was washed with ethyl acetate. The aqueous layer was acidified with hydrochloric acid and extracted with ethyl acetate. The extract was washed with a saturated sodium chloride solution and dried over anhydrous sodium sulfate. The solvent was distilled off to obtain yellow crystals, which were chromatographed over 9 g of silica gel and eluted with chloroform/methanol (50/1), thereby obtaining 77 mg (yield: 77%) of (10,11-dihydro-11-oxo dibenzo[b,f]oxepin-2-yl)-acetic acid. This acid was recrystallized from acetone/n-hexane to give colorless crystals having a melting point of 155.7°–157° C.

IR $\nu_{max}^{KBr}$ cm$^{-1}$: 1710, 1685 (C=O).

NMR (CDCl$_3$+CD$_3$OD)δ: 3.50 (2H, s, —C$\underline{H}_2$—), 3.96 (2H, s, —C$\underline{H}_2$—), 7.09–7.45 (6H, m, aromatic protons), 7.78 (1H, d, J=2H$_3$, C$_1$H).

MS m/e: 268 (M+).

EXAMPLE 9

Ethyl(10,11-dihydro-11-oxo dibenzo[b,f]oxepin-2-yl)-acetate

To 72 mg of (10,11-dihydro-11-oxo dibenzo[b,f]oxepin-2-yl)-acetic acid was added 10 ml of ethanol containing 10% hydrochloric acid, and the mixture was stirred under a dry atmosphere at room temperature for 13 hours. The solent was distilled off under reduced pressure to obtain a residue, which was dissolved in ethyl acetate. The resulting solution was washed with a saturated sodium hydrogen carbonate solution and then with a saturated sodium chloride solution and dried over anhydrous sodium carbonate. The solvent was removed by distillation to obtain 64 mg of a light yellow oil, which was chromatographed over 3.2 g of silica gel and eluted with chloroform, thereby obtaining or yielding 62 mg (yield: 78%) of ethyl(10,11-dihydro-11-oxo dibenzo[b,f]oxepin-2-yl)-acetate as a light yellow oil.

IR $\nu_{max}^{KBr}$ cm$^{-1}$: 1735, 1690 (C=O).

NMR (CDCl$_3$)δ: 1.23 (3H, t, J=7 Hz, —CH$_2$C$\underline{H}_3$), 3.58 (2H, s, —C$\underline{H}_2$COOC$_2$H$_5$), 4.04 (4H, m, —C$\underline{H}$-

$_2$CO— and —COOCH$_2$CH$_3$), 7.20–7.54 (6H, m, aromatic protons), 7.92 (1H, d, J=2 Hz, atomatic proton).

MS m/e: 296 (M+).

EXAMPLE 10

(10,11-Dihydro dibenzo[b,f]oxepin-2-yl)-acetic acid

To 405 mg of (10,11-dihydro-11-oxo dibenzo[b,f]oxepin-2-yl)-acetamide in 10 ml of ethanol was added 1 ml of hydrazine hydrate, and the mixture was refluxed with stirring under a dry atmosphere for 5 hours. The solvent was distilled off under reduced pressure to obtain a residue. To this residue were added 10 ml of diethylene glycol and 2.4 g of sodium hydroxide, and the mixture was stirred under a dry atmosphere at 130° C. for 2 hours. After cooling, to this was added water, and the mixture was washed with ethyl acetate. The aqueous layer was acidified with hydrochloric acid and extracted with ethyl acetate. The extract was washed with a saturated sodium chloride solution and dried over anhydrous sodium sulfate. The solvent was removed by distillation to obtain 392 mg of yellow crystals, which were chromatographed over 30 g of silica gel and eluted with acetone/n-hexane (⅓), thereby yielding 323 mg (yield: 84%) of (10,11-dihydro dibenzo[b,f]oxepin-2-yl)-acetic acid as colorless crystals. The crystals were recrystallized from acetone/n-hexane to give crystals having a melting point of 135°–137° C.

IR $\nu_{max}^{KBr}$ cm$^{-1}$: 1725, (C=O).

NMR (CDCl$_3$)δ: 3.07 (4H, s, —CH$_2$CH$_2$—), 3.51 (2H, s, —CH$_2$COOH), 6.90–7.25 (7H, m, aromatic protons).

MS m/e: 254 (M+).

EXAMPLE 11

Ethyl (10,11-dihydro dibenzo[b,f]oxepin-2-yl)-acetate

To 100 mg of (10,11-dihydro dibenzo[b,f]oxepin-2-yl)-acetic acid was added 10 ml of ethanol containing 10% hydrogen chloride, and the mixture was stirred under a dry atmosphere at room temperature for 4 hours. To this was added ethyl acetate, and the mixture was washed with a saturated sodium chloride solution and dried over anhydrous sodium sulfate. The solvent was distilled off to obtain 100 mg of a pale yellow oil, which was chromatographed over 5 g of silica gel and eluted with chloroform, thereby obtaining 97 mg (yield: 87%) of ethyl(10,11-dihydro dibenzo[b,f]oxepin-2-yl)-acetate as a pale yellow oil.

IR $\nu_{max}^{KBr}$ cm$^{-1}$: 1735, (C=O).

NMR (CCl$_4$)δ: 1.20 (3H, t, J=7 Hz, —CH$_2$CH$_3$), 3.07 (4H, s, —CH$_2$CH$_2$—), 3.36 (2H, s, —CH$_2$COOCH$_2$CH$_3$), 4.01 (2H, q, J=7 Hz, —CH$_2$CH$_3$), 6.82–7.03 (7H, m, aromatic protons).

MS m/e: 282 (M+).

EXAMPLE 12

(10,11-Dihydro dibenzo[b,f]oxepin-2-yl)-acetamide

To 100 mg of (10,11-dihydro dibenzo[b,f]oxepin-2-yl)-acetic acid in 5 ml of dry tetrahydrofuran were added 4 drops of oxalyl chloride, and the mixture was stirred with ice-cooling. To the mixture were added 1 drop of dimethylformamide 1.75 hours later, 4 drops of oxalyl chloride 4 hours later and 1% ammonia in 5 ml tetrahydrofuran 6 hours later, and the resulting mixture was stirred for 17 hours at room temperature. To this was added water, and the mixture was extracted with ethyl acetate. The extract was washed with a 1% sodium hydroxide solution and then with a saturated sodium chloride solution and dried over anhydrous sodium sulfate. The solvent was distilled off under reduced pressure to obtain a residue, which was recrystallized from ethyl acetate to yield 48 mg (yield: 48%) of (10,11-dihydro dibenzo[b,f]oxepin-2-yl)-acetamide as colorless crystals having a melting point of 205°–206° C.

IR $\nu_{max}^{KBr}$ cm$^{-1}$: 3350, 3170 (NH$_2$), 1660 (C=O).

NMR (CDCl$_3$+(CD$_3$)$_2$CO)δ: 3.08 (4H, s, CH$_2$CH$_2$), 3.39 (2H, s, CH$_2$CO), 6.90–7.35 (7H, m, aromatic protons).

EXAMPLE 13

(5,6-Dihydro-6-oxo benzo[b]pyrido[3,2-f]thiepin-8-yl)-acetamide

A mixture of 0.3 g of 2-(4-cyanomethylphenylthio)-3-pyridylacetic acid and 5 g of polyphosphoric acid was stirred at 150°–160° C. for 2.5 hours. After the completion of the reaction, to this was added ice water to decompose excess polyphosphoric acid, and the resulting mixture was basified with an ammonia solution and extracted with chloroform. The extract was washed with a 5% sodium hydrogen carbonate solution and then with water and dried over anhydrous sodium sulfate. The solvent was distilled off to obtain a solid, which was recrystallized from ethanol, thereby yielding 190 mg (yield: 63%) of (5,6-dihydro-6-oxo benzo[b]pyrido[3,2-f]thiepin-8-yl)-acetamide as a light brown powder having a melting point of 215°–216° C.

IR $\nu_{max}^{KBr}$ Cm$^{-1}$: 3400 (NH), 1600 (C=O).

NMR (DMSO-d$_6$)δ: 3.46 (2H, s, —CH$_2$—), 4.27 (2H, s, —CH$_2$—), 7.30–8.04 (5H, m, aromatic protons), 8.37 (1H, d, J=4 Hz, C=H).

MS m/e: 284 (M+).

EXAMPLE 14

(5,6-Dihydro-6-oxo benzo[b]pyrido[3,2-f]thiepin-8yl)-acetic acid

A mixture of 50 mg of (5,6-dihydro-6-oxo benzo[b]pyrido-[3,2-f]thiepin-8-yl)-acetamide, 200 mg of potassium hydroxide, 2 ml of water and 15 ml of methanol was refluxed under a nitrogen atmosphere for 4 hours. After the completion of the reaction, the solvent was distilled off to obtain a residue, to which was added ice water. The mixture was acidified with acetic acid and extracted with chloroform. The extract was washed with water and dried over anhydrous sodium sulfate. The solvent was removed by distillation to obtain an oil, which was chromatographed over silica gel and eluted with chloroform/ethanol (200/1) to obtain a solid. This solid was recrystallized from ethanol to give 15 mg (yield: 30%) of (5,6-dihydro-6-oxo benzo[b]pyrido[3,2-f]thiepin-8-yl)-acetic acid as colorless needle crystals having a melting point of 212°–213.5° C.

IR $\nu_{max}^{KBr}$ Cm$^{-1}$: 1710, 1670 (C=O).

NMR (DMSO-d$_6$)δ: 3.64 (2H, s, —CH$_2$—), 4.27 (2H, s, —CH$_2$—), 7.30–8.04 (5H, m, aromatic protons), 8.37 (1H, d, J=4 Hz, C$_2$H).

MS m/e: 285 (M+).

EXAMPLE 15

Methyl (5,6-dihydro-6-oxo benzo[b]pyrido[3,2-f]thiepin-8-yl)-acetate

To 30 mg of (5,6-dihydro-6-oxo benzo[b]pyrido[3,2-f]thiepin-8-yl)-acetic acid in 5 ml of ethanol was slowly dropped an ether solution containing diazomethane at 0° C. for 2 minutes, and acetic acid was added to decompose excess reagents.

To this was added water, and the mixture was extracted with chloroform. The extract was washed with a 5% sodium hydrogen carbonate solution and then with a saturated sodium chloride solution and dried over anhydrous sodium sulfate. The solvent was distilled off to obtain a residue, which was chromatographed over silica gel and eluted with benzene/chloroform (4/1) to obtain a solid. This was recrystallized from benzene/n-hexane to give 24 mg (yield: 76%) of methyl(5,6-dihydro-6-oxo benzo[b]pyrido[3,2-f]thiepin-8-yl)-acetate as colorless needle crystals having a melting point of 147.5°–149° C.

IR $\nu_{max}^{KBr}$ cm$^{-1}$: 1730, 1665 (C=O).

NMR (CDCl$_3$)δ: 3.64 (2H, s, —C$\underline{H}_2$COOCH$_3$), 3.68 (3H, s, —COOC$\underline{H}_3$), 4.30 (2H, s, —C$\underline{H}_2$CO—), 7.20–7.80 (4H, m, aromatic protons), 8.09 (1H, d, J=2 Hz, aromatic proton), 8.39 (1H, q, J=2 Hz, aromatic proton).

MS m/e: 299 (M+).

EXAMPLE 16

(5,6-Dihydro benzo[b]pyrido[3,2-f]thiepin-8-yl)-acetic acid

A mixture of 400 mg of (5,6-dihydro-6-oxo benzo[b]pyrido[3,2-f]thiepin-8-yl)-acetic acid, 800 mg of hydrazine hydrate and 30 ml of ethanol was refluxed for 3 hours. The solvent was distilled off to obtain a solid substance, to which were added 1 g of sodium hydroxide and 8 ml of diethylene glycol, and the mixture was stirred under a nitrogen atmosphere at 135° C. for 1.5 hours. After cooling, ice water was added to the mixture, and the resulting mixture was acidified with acetic acid and extracted with chloroform. The extract was washed with water and dried over anhydrous sodium sulfate. The solvent was removed by distillation to obtain an oil, which was chromatographed over silica gel and eluted with chloroform ethanol (100/1) to obtain a powder. This was recrystallized from 290 mg (yield: 76%) of (5,6-dihydro benzo[b]pyrido[3,2-f]thiepin-8-yl)-acetic acid as colorless needle crystals.

IR $\nu_{max}^{KBr}$ cm$^{-1}$: 1700 (C=O).

NMR (DMSO-d$_6$)δ: 2.96–3.30 (4H, m, —C$\underline{H}_2$C$\underline{H}_2$—), 3.56 (2H, s, —C$\underline{H}_2$), 6.96–7.54 (5H, m, aromatic protons), 8.22 (1H, d, J=4 Hz, C$_2$H).

MS m/e: 271 (M+).

EXAMPLE 17

(5,6-Dihydro benzo[b]pyrido[3,2-f]thiepin-8yl)-acetamide

A mixture of 100 mg of (5,6-dihydro benzo[b]pyrido[3,2-f]thiepin-8-yl)-acetic acid, 100 mg of dicyclohexylcarbodiimide and 20 ml of chloroform was stirred under a nitrogen atmosphere at 0° C. for 20 minutes. To the resulting mixture was slowly added 1 ml of chloroform containing excess ammonia. The mixture was stirred at 0° C. for 30 minutes and then at room temperature for 1 hour. To this was added 500 g of ice water, and the mixture was acidified with acetic acid and extracted with 50 ml of chloroform. The extract was washed with water, a 5% sodium hydrogen carbonate solution and then with water and dried over anhydrous sodium sulfate. The solvent was distilled off to obtain a residue, to which was added ethyl acetate, and the mixture was filtered to remove any unsoluble substance. Thereafter, the solvent was removed by distillation to obtain a residue, which was chromatographed over silica gel and eluted with chloroform/ethanol (100/1) to obtain a solid. This was recrystallized from benzene/n-hexane to give 24 mg (yield: 24%) of (5,6-dihydro benzo[b]pyrido[3,2-f]thiepin-8-yl)-acetamide as a colorless powder having a melting point of 165°–166° C.

IR $\nu_{max}^{KBr}$ cm$^{-1}$: 3370, 3180 (NH), 1650 (C=O).

NMR (CD$_3$OD)δ: 3.14–3.36 (4H, m, —C$\underline{H}_2$C$\underline{H}_2$—), 3.46 (2H, s, —C$\underline{H}_2$CO—), 7.00–7.52 (5H, m, aromatic protons), 8.14 (1H, d, J=4 Hz, aromatic proton).

MS m/e: 270 (M+).

EXAMPLE 18

Ethyl(5,6-dihydro benzo[b]pyrido[3,2-f]thiepin-8-yl)-acetate

A mixture of 30 mg of (5,6-dihydro benzo[b]pyrido[3,2-f]thiepin-8-yl)-acetic acid, 3 ml of ethanol and 100 mg of sulfuric acid was refluxed for 1 hour. After the completion of the reaction, the solvent was distilled off to obtain a residue, to which was added ice water, and the mixture was basified with a 5% sodium hydrogen carbonate solution and extracted with ethyl acetate. The extract was washed with water and dried over anhydrous sodium sulfate. The solvent was removed by distillation to obtain an oil, which was chromatographed over silica gel and eluted with benzene/chloroform (2/1), thereby yielding 28 mg (yield: 85%) of ethyl (5,6-dihydro benzo[b]pyrido[3,2-f]thiepin-8-yl)-acetate as an oil.

IR $\nu_{max}^{CCl_4}$ cm$^{-1}$: 1740 (C=O).

NMR (CCl$_4$)δ: 1.22 (3H, t, J=7 Hz, —CH$_2$C$\underline{H}_3$), 2.94–3.32 (4H, m, —C$\underline{H}_2$C$\underline{H}_2$—), 3.46 (2H, s, —C$\underline{H}_2$—), 4.07 (2H, q, J=7 Hz, —C$\underline{H}_2$CH$_3$), 6.76–7.48 (5H, m, aromatic protons), 8.14 (1H, d, J=4 Hz, C$_2\underline{H}$).

MS m/e: 299 (M+).

EXAMPLE 19

(5,6-Dihydro-6-oxo benzo[b]pyrido[3,2-f]oxepin-8-yl)-acetamide

To 1 g of 2-(4-cyanomethylphenoxy)-3-pyridylacetic acid was added 20 g of polyphosphoric acid, and the mixture was stirred in an oil bath at 151°–152° C. for 2.5 hours. After cooling, to this ice water was added to decompose excess polyphosphoric acid, and the mixture was basified with a 10% sodium hydroxide solution and extracted with ethyl acetate. The extract was washed with water and then a saturated sodium chloride solution and dried over anhydrous sodium sulfate. The solvent was removed by distillation to obtain a solid, which was chromatographed over 20 g of silica gel and eluted with n-hexane/acetone (2/1–1/1) to obtain crystals. These were recrystallized from acetone to give 300 mg (yield: 30%) of (5,6-dihydro-6-oxo benzo[b]pyrido-[3,2-f]oxepin-8-yl)-acetamide as white needle crystals having a melting point of 214°–217° C.

IR $\nu_{max}^{KBr}$ cm$^{-1}$: 3320, 3180 (NH$_2$), 1680 (C=O).

NMR (DMSO-d$_6$)δ: 3.35 (2H, s, —C$\underline{H}_2$CONH$_2$), 4.05 (2H, s, —C$\underline{H}_2$CO), 6.70 (2H, broad s, —N$\underline{H}_2$), 7.00–8.20 (6H, m, aromatic protons).

MS m/e: 268 (M$^{30}$), 269(M+1).

EXAMPLE 20

(5,6-Dihydro-6-oxo benzo[b]pyrido[3,2-f]oxepin-8-yl)-acetic acid

To 50 mg of (5,6-dihydro-6-oxo benzo[b]pyrido[3,2-f]oxepin-8-yl)-acetamide was added 0.4 g of potassium hydroxide in 4 ml of water/ethanol (1:1), and the mixture was refluxed for 3 hours. After cooling, to this was added water, and the mixture was washed with ethyl acetate. The aqueous layer was acidified with acetic acid and extracted with ethyl acetate. The extract was washed with water and then a saturated sodium chloride solution and dried over anhydrous sodium sulfate. The solvent was distilled off to obtain a solid, which was recrystallized from acetone to give 37 mg (yield: 72%) of (5,6-dihydro-6-oxo benzo[b]pyrido[3,2-f]oxepin-8-yl)-acetic acid as white needle crystals having a melting point of 181°–184° C.

IR $\nu_{max}^{KBr}$ cm$^{-1}$: 1690 (C=O).

NMR (DMSO-d$_6$-CDCl$_3$): 3.55 (2H, s, —CH$_2$COOH), 4.05 (2H, s, —CH$_2$CO), 7.20–8.25 (6H, m, aromatic protons).

MS m/e: 269 (M+), 270 (M+1).

EXAMPLE 21

(5,6-Dihydro benzo[b]pyrido[3,2-f]oxepin-8-yl)-acetic acid

A mixture of 20 mg of (5,6-dihydro-6-oxo benzo[b]pyrido[3,2-f]oxepin-8-yl)-acetamide, 0.5 ml of hydrazine hydrate and 1.5 ml of ethanol was refluxed for 1 hour. The solvent and excess hydrazine hydrate were removed by distillation to obtain a residue, to which was added ethanol. Thereafter, the solvent was distilled off to obtain a yellow oil, which were added 0.1 g of sodium hydroxide and 3 ml of dry diethylene glycol. The mixture was stirred at 100° C. for 20 minutes and then at 120° C. for 2.5 hours. After cooling, to this was added water, and the mixture was washed with ethyl acetate. The aqueous layer was acidified with acetic acid and extracted with ethyl acetate. The extract was washed with water and a saturated sodium chloride solution and dried over anhydrous sodium sulfate. The solvent was distilled off to obtain a solid, which was chromatographed over 1 g of silica gel and eluted with chloroform, thereby yielding 3.5 mg (yield: 18%) of (5,6-dihydro benzo[b]pyrido[3,2-f]oxepin-8-yl)-acetic acid as white needle crystals having a melting point of 203°–204° C.

IR $\nu_{max}^{KBr}$ cm$^{-1}$: 1710 (C=O).

NMR (DMSO-d$_6$-CDCl$_3$)δ: 3.10 (4H, s, —CH$_2$CH$_2$—), 3.50 (2H, s, —CH$_2$COOH), 7.05–8.20 (6H, m, aromatic protons).

EXAMPLE 22

Ethyl(5,6-dihydro benzo[b]pyrido[3,2-f]oxepin-8-yl)-acetate

To a mixture of 20 mg of (5,6-dihydro benzo[b]pyrido[3,2-f]oxepin-8-yl)-acetic acid and 0.5 ml of ethanol was added 2.5 ml of a saturated hydrogen chloride gas-ethanol solution, and the resulting mixture was stirred at room temperature for 1.5 hours. After the completion of the reaction, this was basified with a saturated sodium hydrogen carbonate solution and extracted with chloroform. The extract was washed with a saturated sodium chloride solution and dried over anhydrous sodium sulfate. The solvent was distilled off to obtain an oil, which was chromatographed over 1 g of silica gel and eluted with benzene/chloroform (9/1–8/1), thereby yielding 18 mg (yield: 81.8%) of ethyl(5,6-dihydro benzo[b]pyrido[3,2f]oxepin-8-yl)-acetate as a colorless oil.

IR $\nu_{max}^{CCl_4}$ cm$^{-1}$: 1740 (C=O).

NMR (CCl$_4$)δ: 1.23 (3H, t, J=8 Hz, —CH$_2$CH$_3$), 3.05 (4H, s, —CH$_2$CH$_2$—), 3.40 (2H, s, —CH$_2$COOCH$_2$CH$_3$), 4.05 (2H, q, J=8 Hz, —CH$_2$CH$_3$), 6.80–8.10 (6H, m, aromatic protons).

EXAMPLE 23

(5,6-Dihydro benzo[b]pyrido[3,2-f]oxepin-8-yl)-acetamide

A mixture of 40 mg of (5,6-dihydro benzo[b]pyrido[3,2-f]oxepin-8-yl)-acetic acid, 60 mg of dicyclohexylcarbodiimide and 2 ml of dry dichloromethane was stirred under ice cooling. To the resulting mixture was added 8 ml of a saturated liquid ammonia-dichloromethane solution, and the mixture was stirred for 3 hours. After the completion of the reaction, this was basified with a saturated sodium hydrogen carbonate solution and extracted with ethyl acetate. The extract was washed with water and then with a saturated sodium chloride solution and dried over anhydrous sodium sulfate. The solvent was distilled off to obtain a light yellow oil, which was chromatographed over 4 g of silica gel and eluted with chloroform/ethyl acetate (10/1–8/2) to obtain crystals. These were recrystallized from ethyl acetate to yield 15 mg (yield: 40%) of (5,6-dihydro benzo[b]pyrido[3,2-f]oxepin-8-yl)-acetamide as light yellow needle crystals having a melting point of 164°–165° C.

IR $\nu_{max}^{KBr}$ cm$^{-1}$: 3320, 3160 (NH$_2$), 1680 (C=O).

NMR (CDCl$_3$)δ: 3.08 (4H, s, —CH$_2$CH$_2$—), 3.48 (2H, s, —CH$_2$CONH$_2$), 5.30–5.50 (2H, broad s, NH$_2$), 7.00–8.10 (6H, m, aromatic protons).

What is claimed is:

1. A compound of the formula,

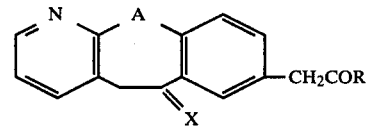

wherein X represents an oxygen or two hydrogen atoms, A represents an oxygen or sulfur atom, and R represents hydroxy, amino or a lower alkoxy group having 1 to 5 carbon atoms.

2. A compound of the formula,

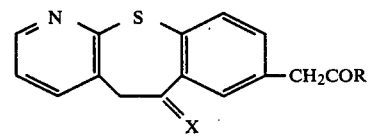

wherein X represents an oxygen or two hydrogen atoms, and R represents hydroxy, amino or a lower alkoxy group having 1 to 5 carbon atoms.

3. A compound of the formula,

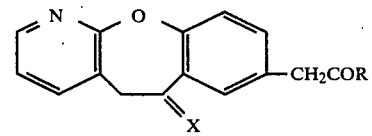

wherein X represents an oxygen or two hydrogen atoms, and R represents hydroxy, amino or a lower alkoxy group having 1 to 5 carbon atoms.

4. A compound of the formula,
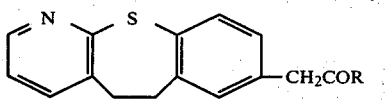
wherein R represents hydrogen, amino or a lower alkoxy group 1 to 5 carbon atoms.
5. A compound of formula,
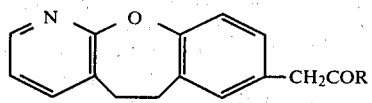
wherein R represents hydrogen, amino or a lower alkoxy group having 1 to 5 carbon atoms.
6. (5,6-Dihydro benzo[b]pyrido[3,2-f]thiepin-8-yl)-acetic acid.
7. 1-5C Lower alkyl (5,6-dihydro benzo[b]pyrido[3,2-f]thiepin-8-yl)-acetate.
8. (5,6-Dihydro benzo[b]pyrido[3,2-f]oxepin-8-yl)-acetic acid.
* * * * *